US00PP32811P3

(12) United States Plant Patent
Maillard et al.

(10) Patent No.: US PP32,811 P3
(45) Date of Patent: Feb. 16, 2021

(54) CHERRY TREE NAMED 'TARDILAM'

(50) Latin Name: ***Prunus avium* (L.) L.**
Varietal Denomination: TARDILAM

(71) Applicant: AGRO SELECTIONS FRUITS, Elne (FR)

(72) Inventors: Laurence Maillard, Elne (FR); Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/602,677

(22) Filed: Nov. 20, 2019

(65) Prior Publication Data

US 2020/0178435 P1 Jun. 4, 2020

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
See application file for complete search history.

(56) References Cited

PUBLICATIONS

CVPO—Community Plant Variety Office—Official Gazette of the Community Plant Variety; Feb. 2019 (3 pages total).*
PLUTO:Plant Variety Database—Retrieved denomination for 'Tardilam' on Oct. 7, 2020.*
www.cpvo.europa.eu "CVPO—Community Plant Variety Office—Help for Community plant variety rights" (10 pages total).*

* cited by examiner

*Primary Examiner* — Susan McCormick Ewoldt
(74) *Attorney, Agent, or Firm* — Birch, Stewart, Kolasch & Birch, LLP

(57) ABSTRACT

A new and distinct variety of cherry tree denominated 'TARDILAM' has fruits with important fruit set, that ripen late to very late in the season, with large size and homogenous bright red fruit skin, very firm, and with a good and semi-sweet to balanced flavor and eating quality; the fruit is further characterized by its good handling and storage qualities.

3 Drawing Sheets

Latin name of the genus and species of the plant claimed: *Prunus avium* (L.) L.

Variety denomination: 'TARDILAM'.

This application claims priority of Community plant variety right No. 2018/3675 filed on Nov. 29, 2018 (Nov. 29, 2018) which is hereby incorporated by reference in its entirety.

The new variety named 'TARDILAM' is also known as 6N.20-2.82.15 CE or ASF1614. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and usually the year of selection. Then before being named 'TARDILAM', the provisional reference of this cherry tree variety was 6N.20-2.82, corresponding to the tree 82 located in line 20-2 of the parcel 6N. The letters "CE" are related to the first letters of the type of tree in French (CE for "CErise", that means "cherry"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'TARDILAM', the clone reference was 'ASF1614'.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary. It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'TARDILAM'. This tree produces fruits with a long shelf life without alteration both on the trees after growth completion and after harvesting, very good eating quality with a cream to slightly yellow colored flesh, and for fresh market in June in the Pyrénées Orientales department, France.

Contrast is made to 'SWEETHEART® SUMTARE' cherry tree (not patented) for reliable description. 'TARDILAM' is a promising candidate for commercial success in that it produces very attractive fruits having a long shelf life.

The present new variety of cherry tree (*Prunus avium* L.) was developed by us in our experimental orchard located in France. 'TARDILAM' cherry tree originated in a cultivated area of the South of France, in the Pyrénées-Orientales department where it was also tested. This zone also called Roussillon is subject to a Mediterranean climate. The winter is generally sweet that is to say the total amount of cold hours lower than 7° C. (Celsius) varies from 600 hours to 1200 hours. The summer is hot and dry, that is to say the total amount of sunshine hours is an average of 2400 hours to 2800 hours per year. The prevailing wind is called "Tramontane": it dries the air and clear the sky from clouds, but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen, and the summer is dry with a few thunderstorms.

The 'TARDILAM' variety resulted from a from pollinated cross between the cherry tree named 'FIRELAM' (U.S. Plant Pat. No. 25,564) which was used as the seed parent, or female parent, and the 'SWEETHEART® SUMTARE' variety (not patented) which was used as the pollen parent, or male parent.

The 'TARDILAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

Compared to the fruits produced by the cherry variety named 'SWEETHEART® SUMTARE' (not patented), that show a size usually between 28 and 29 and a weight of approximately 10 grams, the 'TARDILAM' variety produces fruits with bigger size, typically 29-30, and heavier with a weight of approximately 11 grams.

Also, the variety named 'SWEETHEART® SUMTARE' produces firm fruits with a good preservation, whereas the fruits of the new variety 'TARDILAM' are considered very firm, with a very good preservation.

Compared to the cherry variety named 'BURLAT' (not patented), the fruits of 'TARDILAM' usually ripen more than three weeks later, depending on the year. The flesh fruit of 'BURLAT' is considered red, whereas those produced by the 'TARDILAM' variety have a pink red flesh. Moreover, the fruit taste of 'TARDILAM' is more sugary than the fruit taste of 'BURLAT'.

Compared to its seed parent, i.e. the cherry tree named 'FIRELAM' (U.S. Plant Pat. No. 25,564) as set forth above, the fruits of the new variety 'TARDILAM' ripens 10 to 13 later, depending on the year.

Moreover, the new variety 'TARDILAM' is considered as a self-fertile cherry tree, meaning that no pollination needs to be performed through other varieties, contrary to the seed parent 'FIRELAM'.

The color of fruit flesh is pink red for the variety 'TARDILAM', whereas the fruit flesh of 'FIRELAM' is red.

Regarding the fruit skin, the fruits of 'TARDILAM' are colored with a homogenous bright red covering 90 to 100% of the fruit skin surface. In comparison, the fruits of 'FIRELAM' show a dark red skin.

The fruits of 'TARDILAM' are more sugary than those produced by 'FIRELAM'.

SUMMARY OF THE NEW VARIETY

The new variety 'TARDILAM' produces fruits of large size, very firm, with a semi-sweet flavor, low acidity, and colored with a homogenous bright red blush covering 100% of the skin surface. The blooming period is early to medium for the variety, generally at the end of March or early in April. The maturity period is considered late to very late, and generally begins in June, in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
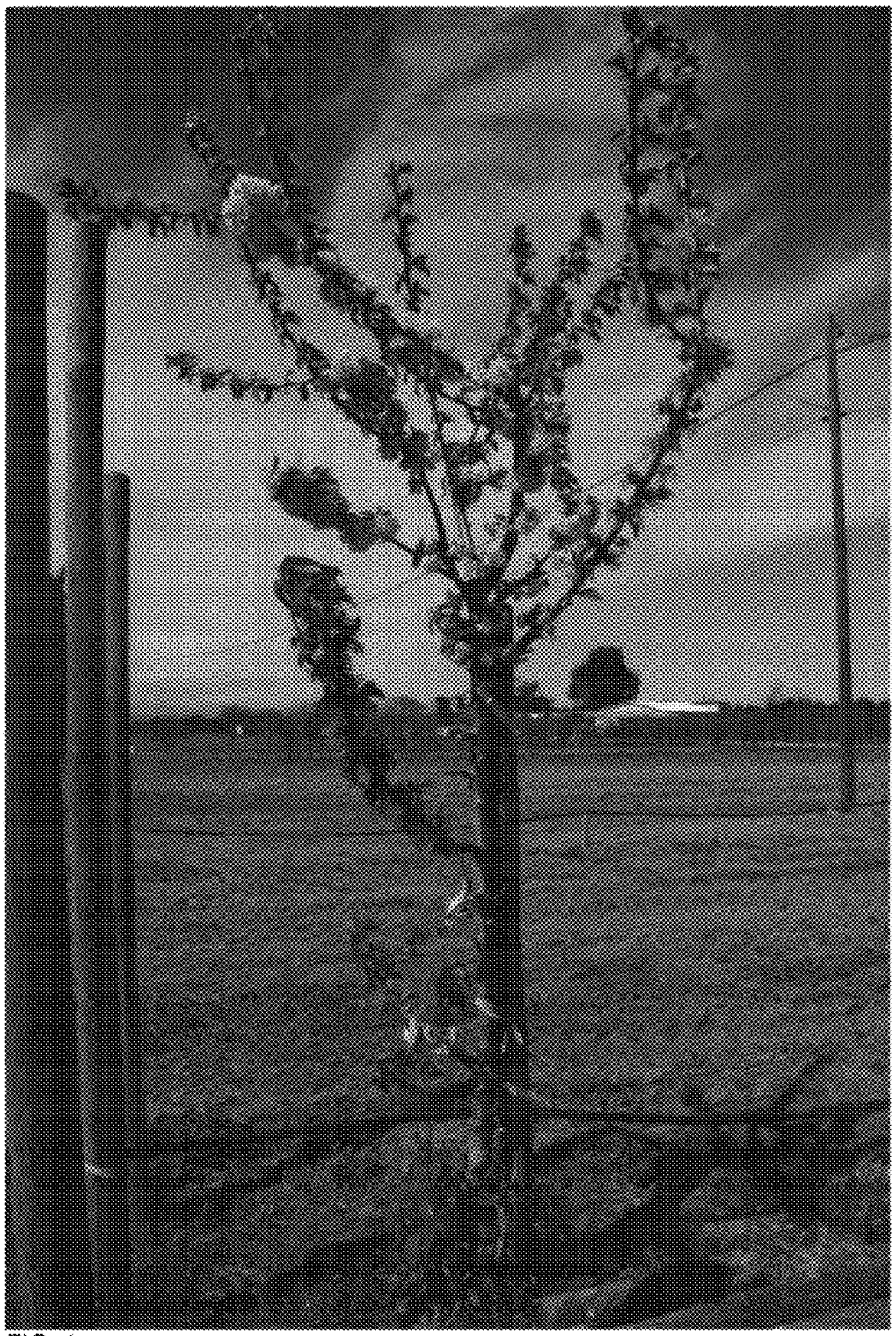
FIG. 1 is a color photograph which shows a view of a tree of the new variety in orchard at blooming time.
Figure 2:
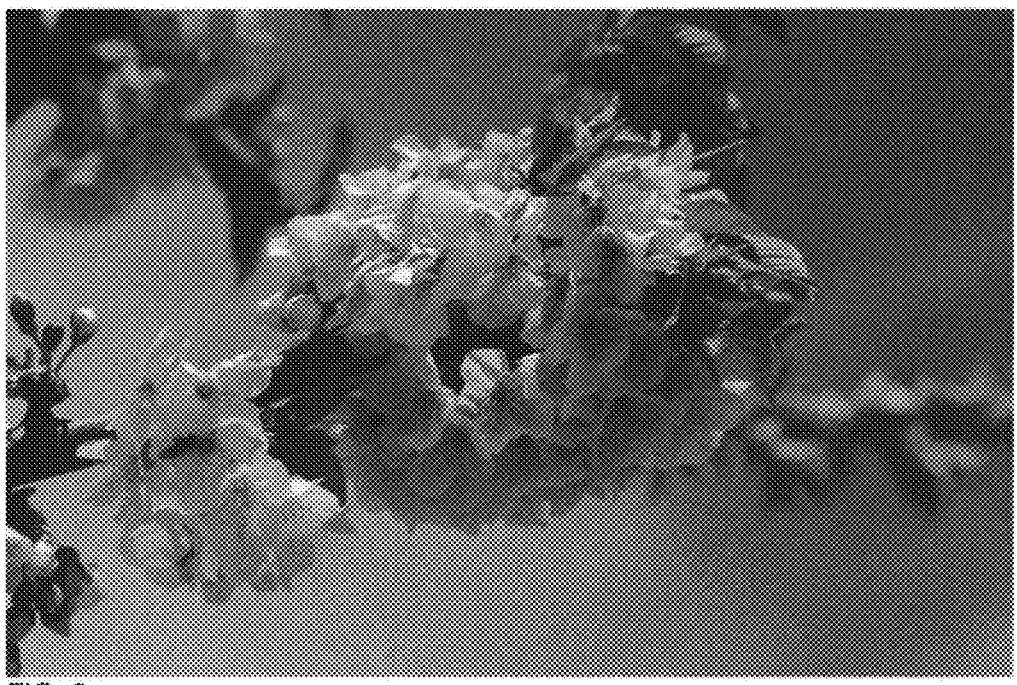
FIG. 2 is a color photograph which shows a close view of a branch of the new variety in orchard at blooming time, with bunches of flowers.
Figure 3:
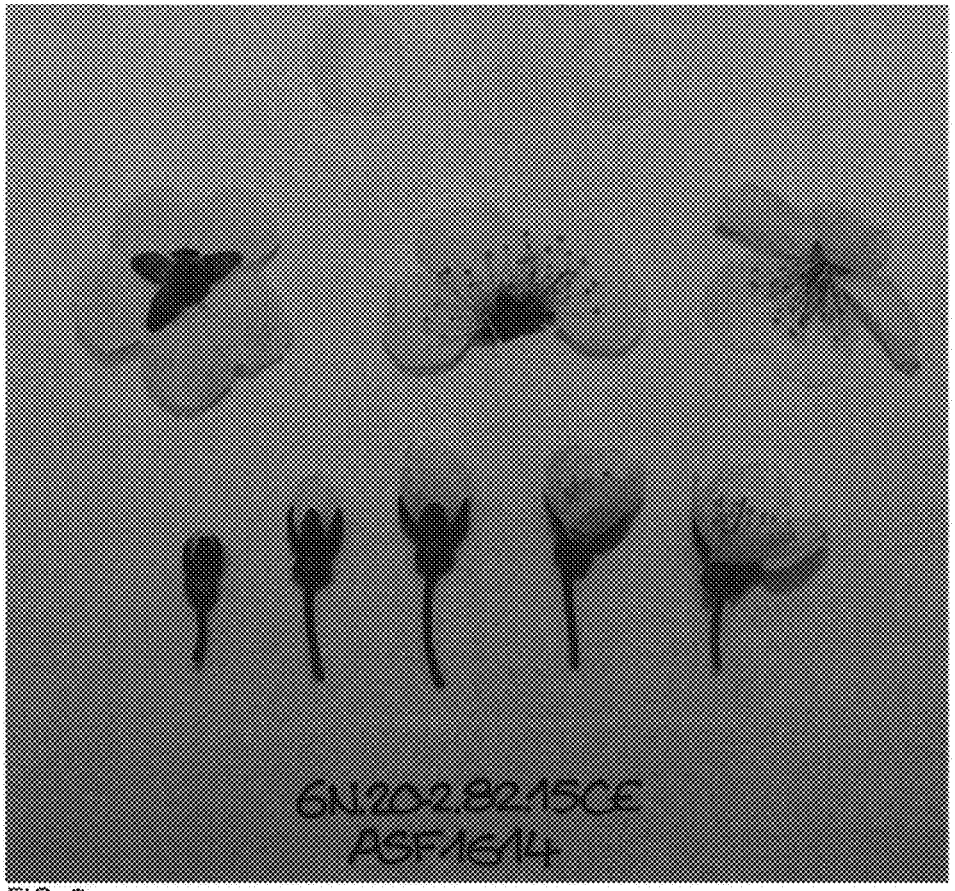
FIG. 3 shows typical white flowers of 'TARDILAM' variety at blooming for depicting the flower buds at different stages of development; and the reverse and side views of the flowers and the reproductive organs with petals removed, of the new variety, also named '6N.20-2.82.15CE ASF 1614'.
Figure 4:
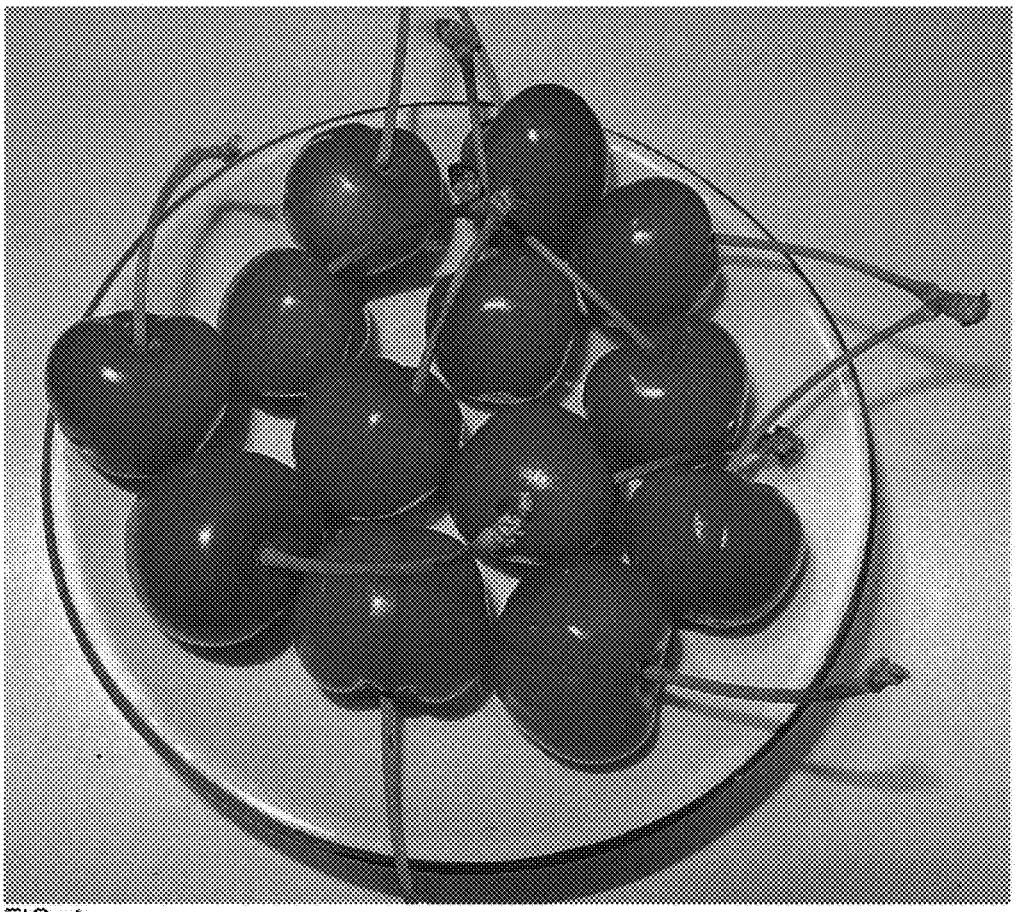
FIG. 4 is a color photograph that shows a close view of typical fruits of the new variety 'TARDILAM' at ripening time.

The enclosed photographs show plants in their fifth growing season (four year of production) for flowers and fruits, and plants in their sixth growing season (five year of production) for trees.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. (Royal Horticultural Society) Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet cherry are a big fruit size with a bright red colored skin. The color of fruit flesh is pink red. The fruit is very firm.

The time of beginning of flowering is early to medium whereas the time of beginning of fruit ripening is considered late to very late.

DETAILED DESCRIPTION

Referring more specifically to the pomological details of this new and distinct variety of cherry tree, the following has been observed on trees on their fifth growing season (four year of production) except for the tree and trunk that have been observed on trees on their sixth growing season (five year of production) under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. (Royal Horticultural Society) Colour Chart 2001 (Fourth Edition) provided by The Royal Horticultural Society of Great Britain.

Tree:

Generally: The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical, and the diameter is limited to 1 meter.

*Size*.—Medium to high as compared to other commercial sweet cherry cultivars. The tree size the first year was approximately 2.50 meters. The tree was pruned during each following dormant season to a height of approximately 2.50 meters. Current season's shoots growth could reach 0.60 to 0.80 meters. So, the tree size from the second year (second and next years) reached a final height of 3.10 to 3.30 meters. The mature branches have been pruned to a length of 30.0 centimeters in order to place nets on the trees.

*Spread*.—Approximately 2.0 meters with a cylindrical shape. The whole orchard was oriented to a central leader organization, with tree lines spaced of 4.0 meters and trees spaced of 1 meter in a same tree line.

*Vigor*.—Medium, tree growth reaching 0.60 to 0.80 meters the first growing season.

*Productivity*.—Good productivity, every year. The new variety produces adequate fruit set annually on a regular basis. The number of the fruit set varies with the prevailing climatic conditions and cultivar practices employed during the bloom period and is therefore not distinctive of the present variety.

*Bearer*.—Very regular and quantitative. The extinction of the clusters of May improves the size and firmness of the fruit.

*Form*.—Semi-spread.

*Hardiness*.—Hardy in all stone fruit growing areas of France and especially where the chilling requirement is between 350 and 1200 hours. No injury with temperatures as low as −12° C. in winter. Good resistance to late frosts. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017,1017 hours in 2017-2018, and 844 hours in 2018-2019 showed a good behavior of the tree in all cases.

Trunk:

*Size*.—Medium. Approximately 74.0 to 79.0 millimeters above 20.0 centimeters from ground, on $6^{th}$ growing season.

*Bark texture*.—Rough with reliefs due to the lenticels.

*Lenticels*.—High number of lenticels. The number of lenticels reaches 10 lenticels per 10 $cm^2$. At the $6^{th}$ growing season, lenticels are 1.5 to 2.0 millimeters in height and 4.5 to 5.5 millimeters in width.

*Lenticels color*.—Color of lenticels is light orange (RHS GREYED ORANGE 164 B or RHS GREYED ORANGE 165 B).

*Bark color*.—Color of bark is brown (RHS BROWN 200 B) to grey (RHS GREY 201 A).

Mature branches:

*Size*.—Medium for the branches at the $6^{th}$ growing season.

*Diameter*.—Average diameter of 9.0 to 11.0 millimeters.

*Crotch angles*.—The crotch angles are generally 70 degrees from the vertical axis. This particular characteristic is not considered distinctive of the variety, however.

*Internode*.—Between 36.0 and 40.0 millimeters.

*Color*.—Old growth is grey (RHS GREY 201 A).

*Surface texture*.—Rough with medium lenticels, similar as bark texture. Wood that is several years old has no furrowed appearance.

*Lenticels*.—The number of lenticels on mature branches reaches 1 lenticel per $cm^2$. The lenticel height is approximately 1.5 millimeter and the lenticel width is approximately 2.5 millimeters. The lenticels are stretched round in shape with a diameter of about 2.5 millimeters.

*Lenticel color*.—The lenticels on mature branches have a beige color (RHS GREYED ORANGE 164 B).

Current season shoots:

*Size*.—Medium for the new growth.

*Diameter*.—Considered medium. Average diameter of about 6.0 to 8.0 millimeters.

*Surface texture*.—Smooth. Wood that is several years old has no furrowed appearance.

*Crotch angles*.—Primary branches are considered variable, but the crotch angles are generally 40 degrees from the vertical axis. This particular characteristic is not considered distinctive of the variety, however.

*Internode*.—Considered short. Generally from 19.0 millimeters to 24.0 millimeters length.

*Color*.—Green (RHS YELLOW GREEN 144 A) to light brown (RHS GREY BROWN 199 A) on lower part of new growth, whereas the upper part is darker and colored in brown (RHS GREY BROWN N199 B).

Leaves:

*Size*.—Medium to large for the species. Leaf measurements have been taken from vigorous, upright, current-season growth at approximately mid-shoot. The ratio leaf length/leaf width is 2.266.

*Length*.—Average length with petiole is 153.33 millimeters.

*Width*.—Average width is 67.67 millimeters.

*Leaf form in cross view*.—Concave.

*Leaf form*.—The form of the leaf is considered entire, with a one-piece limb and without projections of the limb.

*Apex*.—Caudate.

*Leaf base*.—Acute.

*Leaf margins*.—Undulating.

*Leaf margin form*.—The form of the margins is considered crenate.

*Thickness*.—Medium.

*Uniformity*.—Leaves are identical.

*Leaf arrangement*.—Helicoid.

Leaf color:

*Upper leaf surface*.—Green (RHS YELLOW GREEN 147 A).

*Lower surface*.—A lighter green than the upper leaf surface (RHS YELLOW GREEN 146 A or RHS YELLOW GREEN 147 B).

*Leaf texture*.—Both surfaces of leaves are smooth, without any pubescence.

*Leaf venation*.—Pinnately veined.

Mid-vein:

*Width*.—Approximately 2.0 millimeters.

*Color*.—Light green (RHS YELLOW GREEN 145 A) and evolves with maturity.

Secondary veins:

*Color*.—Green (RHS YELLOW GREEN 144 A).

Leaf petioles:

*Size*.—Considered medium to large.

*Length*.—About 39.0 to 47.0 millimeters.

*Diameter*.—About 2.0 to 2.5 millimeters.

*Texture*.—The surface of the petiole is striped on its entire length. Color. The upper surface of petiole is considered purple to brown (RHS GREYED PURPLE N186 C) whereas the lower surface is green (RHS YELLOW GREEN 146 B to RHS YELLOW GREEN 146 C).

*Ratio blade length/petiole length*.—More or less 3.0.

Leaf glands:

*Size*.—Considered medium.

*Length*.—The length of leaf glands is about 3.0 millimeters.

*Width*.—The width of leaf glands is about 2.0 millimeters

*Number*.—Generally 2.

*Type*.—Reniform.

*Margins*.—Smooth and regular.

*Position*.—Alternate on the upper part of petiole.

*Color*.—On young leaves, the leaf glands are colored in orange red (RHS ORANGE RED N34 A). On older leaves, leaf gland color is considered brown (RHS BROWN 200 A), depending on the leaf age.

Leaf stipules:

*Generally*.—No leaf stipules were observed.

Flowers:

Flower buds:

*Generally*.—At pre-floral stage of development, the floral bunches are made up with 3 to 4 floral buds having a round shape with a round tip. Their form is evolving until blooming, with variables dimensions. Then, just before blooming, floral buds show a width comprised between 8.0 and 9.0 millimeters and are approximately 17.0 to 18.0 millimeters long.

*Distribution of flower buds*.—The distribution of the flower buds is considered homogenous on the trees.

*Color*.—This characteristic is dependent upon the proximity to bloom. At pre-floral stage of development, the bottom of the flower's buds, or calyx, or flower receptacle, is of green (RHS YELLOW GREEN 144 B to RHS YELLOW GREEN 144 C) to slightly brown color (RHS GREYED ORANGE 166 B or RHS GREYED ORANGE 166 C) at the outer surface. The inner surface of the calyx is considered greenish yellow (RHS YELLOW GREEN 153 A or RHS YELLOW GREEN 153 B). Above the calyx, the corolla, formed by petals, is generally pure white (RHS WHITE 155 D) on both upper and lower surfaces.

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally late March or early in April. The first bloom was observed from April 7$^{th}$ until Apr. 15, 2016. Then, next bloom took place from March 20$^{th}$ until Mar. 30, 2017, and then from April 2$^{nd}$ until Apr. 12, 2018.

*Blooming time*.—Considered early to medium relative comparison to other commercial cherry cultivars grown in the Pyrénées-Orientales department, France. The date of full bloom is observed at the middle of the blooming period. The date of bloom varies slightly with climatic conditions and cultural practices.

*Blooming period*.—Approximately 9 to 11 days. This characteristic varies slightly with the prevailing climatic conditions.

*Flower type*.—The variety is considered to have a showy type flower (rosette).

*Flower size*.—Considered medium. Average diameter between 34.0 and 36.0 millimeters when totally opened.

*Bloom quantity*.—Considered abundant or very abundant, between 230 and 280 flowers per meter.

*Flower bud frequency*.—Generally 3 to 4 flower buds appear per node.

*Fragrance*.—Soft.

Petal:

*Size*.—Considered medium for the species.

*Length*.—Generally between 16.0 and 17.0 millimeters.

*Width*.—Generally between 14.0 and 15.0 millimeters.

*Petal form*.—Round.

*Petal count*.—Usually 5.

*Petal texture*.—Both petal surfaces have a smooth texture.

*Petal margins*.—Slightly undulated.

*Petal apex*.—The petal apex has a wide dome shaped.

*Petal color*.—Pure white color (RHS WHITE 155 D) on both surfaces.

*Fragrance*.—Very soft.

*Arrangements of petals*.—Intermediate.

Petal claw:

*Form*.—The claw is considered to have a narrow form.

*Length*.—Approximately 1.0 to 1.5 millimeters.

*Width*.—Approximately 1.5 millimeters.

*Color*.—White (RHS WHITE 155 D).

Flower pedicel:

*Length*.—Considered medium to long and having an average length of approximately 17.0 to 21.0 millimeters.

*Diameter*.—Average 1.0 to 1.5 millimeters.

*Color*.—Green (RHS YELLOW GREEN 144 A).

Calyx:

*Internal surface texture*.—Smooth.

*Color*.—At the stage F of blooming, when the flower is open, the inner surface of the calyx, or flower receptacle, is of greenish yellow color (RHS YELLOW GREEN N144 A or RHS YELLOW GREEN 151 A). The outer surface of the calyx is also considered green (RHS YELLOW GREEN 145 A) or brown color (RHS GREYED ORANGE 175 A).

Sepals:

*Surface texture*.—The outer and inner surfaces of the sepals have a smooth texture.

*Size*.—Usually considered medium.

*Length*.—Approximately 6.0 to 7.0 millimeters.

*Width*.—Approximately 4.0 to 5.0 millimeters.

*Shape*.—Conic with a round tip.

*Color*.—The upper surface is green (RHS YELLOW GREEN 144 B to RHS YELLOW GREEN 144 C) or brown color (RHS GREYED ORANGE 175 A). The lower surface of the sepals is considered green color (RHS YELLOW GREEN 144 B to RHS YELLOW GREEN 144 C).

*Number of sepals*.—Generally 5, no overlapping.

*Sepal margins*.—Smooth.

Stamens:

*Average number of stamens per flower*.—Between 29 and 32 stamens per flower.

*Stamen*.—Size compared to petals. The size of stamens is smaller than the size of petals.

*Length*.—Approximately 10.0 to 12.0 millimeters, generally equivalent to pistil's length or slightly smaller, when considered without the ovary.

*Color*.—White (RHS WHITE 155 B or RHS WHITE 155 C).

Anthers:

*Length*.—Medium.

*Diameter*.—Approximately 1.0 millimeter.

*Form*.—Cordate.

*Color*.—Yellow color (RHS YELLOW 11A). The color evolves with flowering.

*Pollen production*.—Pollen is abundant and has a yellow color (RHS YELLOW 11 A) that varies with maturity. The fertility has been checked and the 'TARDILAM' variety is self-fertile (or self pollinating).

Pistil:

*Number*.—Usually 1.

*Length*.—Approximately from 15.0 to 16.0 millimeters including the ovary, that is equivalent to stamens length or slightly higher.

*Color*.—Considered green (RHS YELLOW GREEN 145 B or RHS YELLOW GREEN 145 C). The color may evolve with flowering.

*Surface texture*.—Glabrous.

*Pubescence*.—Absent.

*Stigma*.—Approximately 1.0 millimeter in diameter, with an elliptic shape and a greenish yellow color (RHS YELLOW GREEN N 144 A).

*Ovary*.—Approximately 2.5 to 3.0 millimeters in height. The diameter of the ovary is about 1.5 to 2.0 millimeters. The color is considered green (RHS YELLOW GREEN 144 A).

Type of reproduction: Self-pollination.

Pollinator: This variety is self-fertile so no need to be pollinated by other cherry varieties.

Fruits:

*Maturity when described*.—Very firm at maturity.

*Date of first picking*.—Jun. 13, 2015. The date of picking varies slightly with climatic conditions.

*Date of last picking*.—Last known picking times carry on from June 13$^{th}$ to Jun. 17, 2015, then from June 18$^{th}$ to Jun. 24, 2017, then from June 6$^{th}$ to Jun. 12, 2018.

*Ripening period*.—The 'TARDILAM' variety has a late to very late date time of beginning of fruit ripening. The ripening period lasts approximately 5 to 7 days.

Size:

*Generally*.—Considered large, with a homogeneous size between them, size 29-30.

*Average cheek diameter*.—About 24.0 to 26.0 millimeters.

*Average axial diameter*.—About 28.0 to 30.0 millimeters.

*Typical weight*.—Generally about 11.0 grams. The medium weight is approximately 10.7 grams. This characteristic is highly dependent upon the prevailing cultural practices, and therefore is not particularly distinctive of the variety.

Fruit form:

*Generally*.—Reniform to round.

*Fruit suture*.—Absent.

Ventral surface:

*Form*.—Smooth.

*Apex*.—Slightly in depression.

*Base*.—Slightly in depression.

*Stem cavity*.—Flared and shallow. Average depth of the stem cavity is 0.81 to 1.1 millimeters. Average width is about 6.0 to 7.0 millimeters.

Fruit skin:

*Thickness*.—Considered medium thick and strong.

*Tenacity*.—The adherence of skin to flesh is considered strong, depending on maturity stage.

*Texture*.—Smooth and glabrous.

*Taste*.—Semi-sweet.

*Tendency to crack*.—None.

Color:

*Blush color*.—The fruit skin is colored with a homogenous bright red (RHS RED 46 A) covering 90 to 100% of the fruit skin surface.

Fruit stem:

*Size*.—Medium for the variety.

*Length*.—Approximately 34.0 millimeters.

*Diameter*.—Average diameter is 1.5 millimeters.

*Color*.—Light green (RHS YELLOW GREEN 144 A).

Flesh:

*Ripens*.—Homogenously and slowly. The flesh has a long shelf life.

*Texture*.—Considered dense, crunchy and melting.

*Fibers*.—No fibers.
*Firmness*.—Considered firm to very firm.
*Aroma*.—Good presence
*Eating quality*.—Good to very good. The taste is considered semi-sweet.
*Flavor*.—Semi-sweet, aromatic. Low acidic level.
*Juice*.—Good amount.
*Brix*.—Between 17.0 and 18.5 with a medium Brix of approximately 18.0 varies slightly with amount of fruit per tree and climatic conditions.
*Color of juice*.—Pink color (RHS RED 36 A).
*Color of flesh*.—Pink red (RHS ORANGE RED N34 A) and the color of flesh in the stone cavity and around the stone cavity is similar.

Stone:
*Type*.—Freestone at fruits picking.
*Size*.—Small to medium for the variety.
*Length*.—Approximately 10.0 millimeters.
*Width*.—Approximately 8.0 millimeters.
*Diameter*.—Approximately 6.0 millimeters.
*Form*.—Round.
*Base*.—Generally round.
*Apex*.—Round.
*Stone color*.—The color of the dry stone is beige (RHS GREYED YELLOW 161 D).
*Stone cavity*.—Small to medium, with a form and dimensions corresponding to the stone's dimensions.

Stone surface:
*Surface texture*.—Smooth.
*Ridges*.—None, smooth.
*Tendency to split*.—Splitting is absent.

Ventral edge:
*Width*.—Very shallow, more or less 0.5 millimeter.

Dorsal edge:
*Shape*.—Full, without any relief.
*Tendency to split*.—None.

Kernel:
*Size*.—Small.
*Length*.—Approximately 7.0 millimeters.
*Width*.—Approximately 5.0 millimeters.
*Thickness*.—Approximately 4.0 millimeters.
*Form*.—Round.
*Pellicle*.—Not pubescent, smooth.
*Color*.—The kernel skin is light cream (RHS GREYED YELLOW 162 C). The almond, which is the seed of the kernel, is white (RHS WHITE 155 D) and has a bitter taste. The kernel and its embryo are mature at the time of fruit maturity.

Use: Dessert. Fresh products.
*Market*.—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run and 'TARDILAM' variety seems to be low sensitive to pathologies, to rupture and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of cherry tree, substantially as illustrated and described, characterized by its important fruit set, its late to very late ripening, its fruits and especially by its large size, its homogenous bright red fruit skin, its important firmness, good and semi-sweet flavor and eating quality; the fruit is further characterized by its good handling and storage qualities.

* * * * *